(12) United States Patent
McLaughlin (10) Patent No.: US 11,576,619 B2
(45) Date of Patent: Feb. 14, 2023

(54) PREDICTIVE USE OF QUANTITATIVE IMAGING

(71) Applicant: Shenzhen Mindray Bio-Medical Electronics Co., Ltd., Shenzhen (CN)

(72) Inventor: Glen W. McLaughlin, San Carlos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/501,280

(22) Filed: Oct. 14, 2021

(65) Prior Publication Data
US 2022/0087616 A1 Mar. 24, 2022

Related U.S. Application Data

(63) Continuation of application No. 16/870,364, filed on May 8, 2020, now Pat. No. 11,213,257, which is a
(Continued)

(51) Int. Cl.
*G06V 10/00* (2022.01)
*A61B 5/00* (2006.01)
(Continued)

(52) U.S. Cl.
CPC .......... *A61B 5/7267* (2013.01); *A61B 5/0035* (2013.01); *A61B 5/0048* (2013.01);
(Continued)

(58) Field of Classification Search
CPC .. G06K 9/6201; G06K 9/6267; G06K 9/6218; G06K 9/6229; G06K 9/6255; G06K 9/6269; G06K 9/6282; A61B 5/7267; A61B 5/0035; A61B 5/0048; A61B 5/0095; A61B 5/021; A61B 5/024; A61B 5/055; A61B 5/4277; A61B 5/4842; A61B 5/4866;
(Continued)

(56) References Cited

U.S. PATENT DOCUMENTS

| | | | | |
|---|---|---|---|---|
| 4,331,021 A | * | 5/1982 | Lopez | G01S 7/52052 73/1.86 |
| 4,633,715 A | * | 1/1987 | Monchalin | G01N 29/2418 356/486 |

(Continued)

*Primary Examiner* — Amir Alavi
(74) *Attorney, Agent, or Firm* — Kory D. Christensen (57) ABSTRACT

The present disclosure provides systems and methods for predicting a disease state of a subject using ultrasound imaging and ancillary information to the ultrasound imaging. At least two quantitative measurements of a subject, including at least one measurement taken using ultrasound imaging, as part of quantified information can be identified. One of the quantitative measurements can be compared to a first predetermined standard, included as part of ancillary information to the quantified information, in order to identify a first initial value. Further, another of the quantitative measurements can be compared to a second predetermined standard, included as part of the ancillary information, in order to identify a second initial value. Subsequently, the quantitative information can be correlated with the ancillary information using the first initial value and the second initial value to determine a final value that is predictive of a disease state of the subject.

20 Claims, 4 Drawing Sheets

Related U.S. Application Data continuation of application No. 15/928,921, filed on Mar. 22, 2018, now Pat. No. 10,682,098.

(51) Int. Cl.

| | |
|---|---|
| *A61B 8/08* | (2006.01) |
| *A61B 5/021* | (2006.01) |
| *A61B 5/024* | (2006.01) |
| *A61B 6/00* | (2006.01) |
| *A61B 6/03* | (2006.01) |
| *A61B 5/055* | (2006.01) |
| *G06K 9/62* | (2022.01) |
| *G06T 7/00* | (2017.01) |
| *A61B 8/15* | (2006.01) |

(52) U.S. Cl.
CPC .......... *A61B 5/0095* (2013.01); *A61B 5/021* (2013.01); *A61B 5/024* (2013.01); *A61B 5/055* (2013.01); *A61B 5/4277* (2013.01); *A61B 5/4842* (2013.01); *A61B 5/4866* (2013.01); *A61B 5/4872* (2013.01); *A61B 6/032* (2013.01); *A61B 6/485* (2013.01); *A61B 6/504* (2013.01); *A61B 8/15* (2013.01); *A61B 8/481* (2013.01); *A61B 8/488* (2013.01); *G06K 9/6218* (2013.01); *G06K 9/6229* (2013.01); *G06K 9/6255* (2013.01); *G06K 9/6269* (2013.01); *G06K 9/6282* (2013.01); *G06T 7/0014* (2013.01); *G06T 2207/10081* (2013.01); *G06T 2207/10088* (2013.01); *G06T 2207/10132* (2013.01); *G06T 2207/20081* (2013.01); *G06T 2207/20084* (2013.01); *G06T 2207/30056* (2013.01); *G06T 2207/30068* (2013.01); *G06T 2207/30081* (2013.01)

(58) Field of Classification Search
CPC ....... A61B 5/4872; A61B 6/032; A61B 6/485; A61B 6/504; A61B 8/15; A61B 8/481; A61B 8/488; G06T 7/0014; G06T 2207/10088; G06T 2207/10081; G06T 2207/10132; G06T 2207/20081; G06T 2207/20084; G06T 2207/30056; G06T 2207/30068; G06T 2207/30081

See application file for complete search history.

(56) References Cited

U.S. PATENT DOCUMENTS

| | | | | |
|---|---|---|---|---|
| 5,560,242 | A * | 10/1996 | Flax | G01N 29/30 73/1.82 |
| 5,860,929 | A * | 1/1999 | Rubin | A61B 8/06 600/454 |
| 6,068,598 | A * | 5/2000 | Pan | G01S 15/8984 600/453 |
| 7,037,267 | B1 | 5/2006 | Lipson | |
| 7,204,807 | B2 | 4/2007 | Tsoref | |
| 8,016,757 | B2 * | 9/2011 | Kaczkowski | A61B 8/5223 601/3 |
| 8,079,957 | B2 * | 12/2011 | Ma | A61B 8/483 600/437 |
| 8,192,364 | B2 | 6/2012 | Main et al. | |
| 8,320,996 | B2 | 11/2012 | Panasyuk | |
| 8,512,247 | B2 | 8/2013 | Hill | |
| 8,622,911 | B2 | 1/2014 | Hossack | |
| 8,718,339 | B2 | 5/2014 | Tonomura et al. | |
| 9,301,732 | B2 | 4/2016 | Tonomura et al. | |
| 9,402,601 | B1 * | 8/2016 | Berger | A61B 8/54 |
| 9,415,123 | B2 | 8/2016 | El-Sayed | |
| 9,615,815 | B2 | 4/2017 | Kwartowitz | |
| 9,636,085 | B2 | 5/2017 | Sandrin et al. | |
| 9,888,879 | B1 | 2/2018 | Cho et al. | |
| 9,968,330 | B2 | 5/2018 | Abe et al. | |
| 10,028,700 | B2 | 7/2018 | Sarnow et al. | |
| 10,085,721 | B2 | 10/2018 | Chen | |
| 10,507,315 | B2 | 12/2019 | Hossack | |
| 10,682,098 | B2 * | 6/2020 | McLaughlin | A61B 8/488 |
| 10,959,706 | B2 * | 3/2021 | Suzuki | A61B 6/032 |
| 11,051,790 | B2 | 7/2021 | Wodlinger | |
| 11,213,257 | B2 * | 1/2022 | McLaughlin | G06K 9/6255 |
| 11,331,078 | B2 * | 5/2022 | Labyed | G01S 7/52085 |
| 2012/0059262 | A1 | 3/2012 | Clark | |
| 2017/0173262 | A1 | 6/2017 | Veltz | |
| 2019/0029021 | A1 | 9/2019 | McLaughlin | |

\* cited by examiner

PREDICTIVE USE OF QUANTITATIVE IMAGING

TECHNICAL FIELD

The present disclosure relates to ultrasound imaging.

BACKGROUND OF THE INVENTION

Ultrasound imaging is a widely used for examining a wide range of materials and objects across a wide array of different applications. Ultrasound imaging provides a fast and easy operate tool for analyzing materials and objects in a non-invasive. As a result, ultrasound imaging is especially common in the practice of medicine as an ailment diagnosis, treatment, and prevention tool. Specifically, because of its relatively non-invasive nature, low cost and fast response time ultrasound imaging is widely used throughout the medical industry to diagnose and prevent ailments. Further, as ultrasound imaging is based on non-ionizing radiation it does not carry the same risks as other diagnosis imaging tools, such as X-ray imaging or other types of imaging systems that use ionizing radiation.

Ultrasound imaging is accomplished by generating and directing ultrasonic sound waves into a material of interest, first in a transmit phase and subsequently in a receive phase. During the transmit phase, an ultrasonic signal is transmitted into a material of interest by applying continuous or pulsed electronic signals. During the receive phase, reflections generated by boundaries between dissimilar materials are received by receiving devices, such as transducers, and converted to electrical signals. Signals can then be processed to determine the locations of the echo sources. The resulting data can be used to display images of inside a material of interest, e.g. by displaying images using a display device, such as a monitor.

Ultrasound imaging can offer a wealth of clinical information. Specifically, ultrasound imaging can be used in abdominal ultrasound (to visualize abdominal tissues and organs), bone sonometry (to assess bone fragility), breast ultrasound (to visualize breast tissue), doppler fetal heart rate monitors (to listen to a fetal heart beat), doppler ultrasound (to visualize blood flow through a blood vessel, organs, or other structures), echocardiogram (to view a heart), fetal ultrasound (to view a fetus in pregnancy), utrasound-guided biopsies (to collect a sample of tissue), ophthalmic ultrasound (to visualize ocular structures) and ultrasound-guided needle placement (in blood vessels or other tissues of interest). Ultrasound imaging has also been used in describing various disease states, such as diseases of the liver, breast, prostate, thyroid or other organs through single measurements of stiffness or shear wave velocity.

While ultrasound imaging provides a potential wealth of clinical information, clinicians, doctors, or experts often need to analyze and interpret ultrasound images in order to realize or otherwise identify the wealth of clinical information. Specifically, most ultrasound information is presented to a clinician for visualization in a qualitative manner, e.g. as an actual displayed image. As a clinician is limited in how much information they can interpret and ultrasound imaging, owing to its cheap, fast, and mostly non-invasive nature, produces large amounts of information, compromises must be made on the amount of information that can be presented and subsequently analyzed. For example, an image that indicates a vascular disease is present might not be presented to a clinician, thereby leading to a missed diagnosis.

Further, ultrasound imaging can lead to inconsistent diagnoses and standards of care may also result as a result of differences between clinicians. Other fields of medicine have made attempts to minimize these differences by relying on more quantitative aspects of diagnoses. It is difficult to rely on quantitative aspects of ultrasound because of its qualitative nature and presentation.

There therefore exists a need for incorporating other imaging modalities as well as other physiological measurements into analysis of ultrasound images. More specifically, there exists a need for systems and methods for combining, correlating, or otherwise using ultrasound images, and data associated therewith, and ancillary information to further derive clinical information for ailment diagnosing, treatment, and prevention.

SUMMARY

In various embodiments, quantitative information, such as information which can be derived from ultrasound, and ancillary information, such as diagnosis standards, are correlated and analyzed to predict disease states of an individual or segmented population.

Further in various embodiments, a method of predicting a disease state from two or more quantitative measurements can include taking at least two quantitative measurements indicated by ultrasound imaging data gathered using ultrasound imaging. The method can also include comparing one of the at least two quantitative measurements to a first predetermined standard, included as part of ancillary data to the ultrasound imaging data, to determine an initial value. The first predetermined standard can be within a range of quantities. Further, the method can include comparing another of the at least two quantitative measurements to a second predetermined standard, included as part of the ancillary data to the ultrasound imaging data, to determine a second initial value. The second predetermined standard can be within a range of quantities. The two or more quantitative measurements can be compared to the standards as part of correlating the quantitative data with the ancillary data. Additionally, the method can include combining the first initial value with the second initial value to determine a final value predictive of a disease state.

In various embodiments, quantitative measurements can include an ultrasonic imaging quantitative measurement generated through at least one of contrast-enhanced ultrasound, photo-acoustic imaging, acoustic radiation force impulse imaging, ultrasonic characterization of non-linear properties, ultrasonic attenuation, ultrasonic sound speed characterizations and/or ultrasonic speckle statistics. More specifically, at least one of the quantitative measurements can be a core biopsy measurement, blood pressure measurement, pulse measurement, BMI measurement, body fat measurement, angiography measurement, blood analysis measurement, saliva analysis measurement, photo-acoustic imaging measurement, protein screening and genetic screening measurement.

In various embodiments other imaging modalities can be utilized or otherwise combined with ultrasound imaging to provide analysis, e.g. ailment diagnosis, treatment, and prevention. Other imaging modalities can include one or a combination of core biopsy, X-rays, fluoroscopy, computed tomography, or MRI.

Additionally, in various embodiments raw data can be used with ultrasound imaging to further provide analysis. In various embodiments, a machine-learning algorithm can be used with ultrasound imaging to classify disease states, compare measurements, create predetermined standards, determine initial and final values and/or determine a range of quantities and/or qualities. A machine-learning algorithm can be applied or otherwise maintained through one or a combination of decision tree learning, association rule learning, artificial neural networks, inductive logic, a support vector, clustering, Baysian networks, reinforcement learning, representation learning, similarity and/or metric learning, sparse dictionary learning and/or protein and/or genetic algorithms.

In various embodiments, a method includes taking at least one quantitative measurement to predict a disease state. The quantitative measurement can be compared to a first predetermined standard to determine an initial value. The first predetermined standard can be within a range of quantities. The method can also include taking at least one qualitative measurement and comparing the qualitative measurement to a second predetermined standard to determine a second initial value. The second predetermined standard can be within a range of qualities. Further, the method can include combining the first initial value with the second initial value, e.g. as part of correlating the quantitative measurement and the qualitative measurement, to determine a final value that is predictive of a disease state.

Further, in various embodiments, a method includes taking at least one quantitative measurement to predict a disease state and comparing the one of the at least one quantitative measurements to a first predetermined standard to determine an initial value. The first predetermined standard can be within a range of quantities. The method can also include comparing a previous measurement of disease to a second predetermined standard to determine a second initial value. The second predetermined standard can be within a range of qualities. Further, the method can include combining the first initial value with the second initial value to determine a final value that is predictive of a disease state.

In various embodiments, a previous measurement, e.g. of disease, can include at least one of a biopsy, blood assay, vascularization and/or metabolic rate. Further, in various embodiments, a previous measurement of disease can be determined according to a non-ultrasound method.

DETAILED DESCRIPTION

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are described herein. For purposes of the disclosure, the following terms are used as described below.

As used herein, "acoustic radiation force impulse imaging" or "ARFI" shall mean a type of ultrasound elastography used in medicine. ARFI may be used, for example, for the diagnosis and monitoring of cancers, among other things. ARFI imaging uses acoustic radiation force to generate images of the mechanical properties of soft tissue. momentum As used herein, "angiography" or "arteriography" refers to a medical imaging technique used to visualize the inside, or lumen, of blood vessels and organs of the body, with particular interest in the arteries, veins, and the heart chambers. The technique is traditionally done by injecting a radio-opaque contrast agent into the blood vessel and imaging using X-ray based techniques such as fluoroscopy. Angiography traditionally has been strictly defined as based on projectional radiography. The term recently, however, has also been applied to newer vascular imaging techniques such as CT angiography and MR angiography.

As used herein, "artificial neural networks" or "ANNs" shall refer to a family of models inspired by biological neural networks (the central nervous system of animals, in particular the brain) which are used to estimate or approximate functions that can depend on a large number of inputs.

As used herein, "attenuation" refers to a gradual loss in intensity of any kind of flux through a medium. For instance, dark glasses attenuate sunlight, lead attenuates X-rays, and water attenuates both light and sound. Attenuation in ultrasound is the reduction in amplitude of the ultrasound beam as a function of distance through the imaging medium. Accounting for attenuation effects in ultrasound is important because a reduced signal amplitude can affect the quality of the image produced. By knowing the attenuation that an ultrasound beam experiences traveling through a medium, one can adjust the input signal amplitude to compensate for any loss of energy at the desired imaging depth.

As used herein, a "Bayesian network," "Bayes network," "belief network," "Bayes(ian) model" or "probabilistic directed acyclic graphical model" is a probabilistic graphical model (a type of statistical model) that represents a set of random variables and their conditional dependencies via a directed acyclic graph (DAG). For example, a Bayesian network could represent the probabilistic relationships between diseases and symptoms. Given symptoms, the network can be used to compute the probabilities of the presence of various diseases.

As used herein, a "biopsy" is a medical test commonly performed by a surgeon, interventional radiologist or an interventional cardiologist of some other person that involves an extraction of sample cells or tissues for examination to determine the presence or extent of a disease. The tissue is generally examined under a microscope by a pathologist, and can also be analyzed chemically. When an entire lump or suspicious area is removed, the procedure is called an excisional biopsy. When only a sample of tissue is removed with preservation of the histological architecture of the tissue's cells, the procedure is called an incisional biopsy or core biopsy. When a sample of tissue or fluid is removed with a needle in such a way that cells are removed without preserving the histological architecture of the tissue cells, the procedure is called a needle aspiration biopsy. Biopsies are most commonly performed for insight into possible cancerous and inflammatory conditions.

As used herein, "core biopsy" shall mean a procedure where a special needle (or probe) is inserted into a tissue to take a small sample from an area of concern so that it can be sent to a laboratory for testing. It is done using local anaesthetic to numb the area that is being biopsied. A core needle biopsy is often used where the tissue of interest is the breast.

As used herein, a "blood assay" or "blood test" or any other analogous terms used by one skilled in the art shall mean a laboratory analysis performed on a blood sample taken from a subject.

As used herein "blood pressure" or "BP" shall mean the pressure exerted by circulating blood upon the walls of blood vessels. When used without further specification, "blood pressure" usually refers to the arterial pressure in the systemic circulation. It is usually measured at a person's upper arm. Blood pressure is usually expressed in terms of the systolic (maximum) pressure over diastolic (minimum) pressure and is measured in millimeters of mercury (mm Hg). It is one of the vital signs along with respiratory rate, heart rate, oxygen saturation, and body temperature. Normal resting systolic/diastolic blood pressure in an adult is approximately 120 mm Hg/80 mm Hg, abbreviated "120/80 mm Hg".

Blood pressure varies depending on situation, activity, and disease states. It is regulated by the nervous and endocrine systems. Blood pressure that is low due to a disease state is called hypotension, and pressure that is consistently high is hypertension. Both have many causes which can range from mild to severe. Both may be of sudden onset or of long duration. Long term hypertension is a risk factor for many diseases, including kidney failure, heart disease, and stroke. Long term hypertension is more common than long term hypotension in Western countries. Long term hypertension often goes undetected because of infrequent monitoring and the absence of symptoms.

As used herein, "body mass index" or "BMI" or Quetelet index is a value derived from the mass (weight) and height of an individual. The BMI is defined as the body mass divided by the square of the body height, and is universally expressed in units of $kg/m^2$, resulting from mass in kilograms and height in meters. BMI may also be determined using a table or chart which displays BMI as a function of mass and height using contour lines or colors for different BMI categories, and may use two different units of measurement. The BMI is an attempt to quantify the amount of tissue mass (muscle, fat, and bone) in an individual, and then categorize that person as underweight, normal weight, overweight, or obese based on that value. However, there is some debate about where on the BMI scale the dividing lines between categories should be placed. Commonly accepted BMI ranges are underweight: under 18.5, normal weight: 18.5 to 25, overweight: 25 to 30, obese: over 30.

As used herein, "cluster analysis" or "clustering" refers to the task of grouping a set of objects in such a way that objects in the same group (called a cluster) are more similar (in some sense or another) to each other than to those in other groups (clusters).

As used herein, a "Digital geometry processing" is used to generate a three-dimensional image of the inside of the body from a large series of two-dimensional radiographic images taken around a single axis of rotation.

As used herein, "contrast-enhanced ultrasound" or "CEUS" is the application of ultrasound contrast medium to traditional medical sonography. Ultrasound contrast agents rely on the different ways in which sound waves are reflected from interfaces between substances. This may be the surface of a small air bubble or a more complex structure. Commercially available contrast media are gas-filled microbubbles that are administered intravenously to systemic circulation. Microbubbles have a high degree of echogenicity (the ability of an object to reflect ultrasound waves). There is a great difference in echogenicity between the gas in the microbubbles and the soft tissue surroundings of the body. Thus, ultrasonic imaging using microbubble contrast agents enhances the ultrasound backscatter of the ultrasound waves, to produce a sonogram with increased contrast due to the high echogenicity difference. Contrast-enhanced ultrasound can be used to image blood perfusion in organs, measure blood flow rate in the heart and other organs, and for other applications.

As used herein, "decision tree learning" refers to decision tree predictive modeling decision tree learning, the goal is to create a model that predicts the value of a target variable based on several input variables. A tree can be "learned" by splitting the set subsets based on an attribute value test.

As used herein, "elastography" shall mean a medical imaging modality that maps the elastic properties of soft tissue. Whether or not a tissue is hard or soft will give diagnostic information about the presence or status of disease. For example, cancerous tumors will often be harder than the surrounding tissue, and diseased livers are stiffer than healthy ones.

As used herein, "genetic screening" or "genetic testing" or "DNA testing" each refer to tests that allow the genetic diagnosis of vulnerabilities to inherited diseases, and can also be used to determine a child's parentage (genetic mother and father) or in general a person's ancestry or biological relationship between people. In addition to studying chromosomes to the level of individual genes, genetic testing in a broader sense includes biochemical tests for the possible presence of genetic diseases, or mutant forms of genes associated with increased risk of developing genetic disorders. Genetic testing may identify changes in chromosomes, genes, or proteins. The variety of genetic tests has expanded throughout the years. In the past, the main genetic tests searched for abnormal chromosome numbers and mutations that lead to rare, inherited disorders. Today, tests involve analyzing multiple genes to determine the risk of developing certain more common diseases such as heart disease and cancer. The results of a genetic test can confirm or rule out a suspected genetic condition or help determine a person's chance of developing or passing on a genetic disorder. Several hundred genetic tests are currently in use, and more are being developed.

As used herein, a "hyperplane" is a subspace of one dimension less than its ambient space. If a space is 3-dimensional then its hyperplanes are the 2-dimensional planes, while if the space is 2-dimensional, its hyperplanes are the 1-dimensional lines. This notion can be used in any general space in which the concept of the dimension of a subspace is defined. In different settings, the objects which are hyperplanes may have different properties. For instance, a hyperplane of an n-dimensional affine space is a flat subset with dimension n−1.

As used herein, a "hypervolume" shall refer to a region that has more than three dimensions.

As used herein, "imaging modality" shall mean any of the various types of equipment or probes used to acquire images of the body. Examples include, without limitation, radiography, ultrasound and magnetic resonance imaging or any other of the other methods disclosed herein or know to one skilled in the art.

As used herein, "metabolic rate" shall mean rate of metabolism or the amount of energy expended in a given organism per some unit, such as time. As a non-limiting example, a basic metabolic rate is often measured in an organism and is defined as an estimate of how many calories the organism would burn if it did nothing but rest over some period of time, such as a day. The basic metabolic rate represents the minimum amount of energy needed to keep an organism functioning, including breathing and keeping a heart beating. The basic metabolic rate of an organism may be measured looking specifically for abnormalities such as whether the basic metabolic rate is too high or too low, either measurement being an indication of disease or a disease state. Metabolic rate may also refer to the speed or frequency with which an event or circumstance occurs per unit of time, population, or other standard of comparison such as, for example, the speed of a reaction hi an enzyme or a group of enzymes.

As used herein, "MRI" or "Magnetic resonance imaging," "nuclear magnetic resonance imaging" or "NMRI," "magnetic resonance tomography" or "MRT" shall mean a medical imaging technique used in radiology to image the anatomy and the physiological processes of the body in both health and disease. MRI scanners use strong magnetic fields, radio waves, and field gradients to form images of the body. MRI is based upon the science of nuclear magnetic resonance (NMR). Certain atomic nuclei can absorb and emit radio frequency energy when placed in an external magnetic field. In clinical and research MRI, hydrogen atoms are most-often used to generate a detectable radio-frequency signal that is received by antennas in close proximity to the anatomy being examined. Hydrogen atoms exist naturally in people and other biological organisms in abundance, particularly in water and fat. For this reason, most MRI scans essentially map the location of water and fat in the body. Pulses of radio waves are used to excite the nuclear spin energy transition and magnetic field gradients localize the signal in space. By varying the parameters of the pulse sequence, different contrasts can be generated between tissues based on the relaxation properties of the hydrogen atoms therein. Since its early development in the 1970s and 1980s, MRI has proven to be a highly versatile imaging modality. While MRI is most prominently used in diagnostic medicine and biomedical research, it can also be used to form images of non-living objects. MRI scans are capable of producing a variety of chemical and physical data, in addition to detailed spatial images. MRI is widely used in hospitals and clinics for medical diagnosis, staging of disease and follow-up without exposing the body to ionizing radiation.

As used herein, "photoacoustic imaging" or "optoacoustic imaging" refers to imaging based on the photoacoustic effect. Sound, which propagates as a pressure wave, can be induced in virtually any material, including biologic tissue, whenever time-varying electromagnetic energy is absorbed. The stimulating radiation that induces these thermally generated acoustic waves may lie anywhere in the electromagnetic spectrum, from high-energy ionizing particles to low-energy radio waves. While "photoacoustic imaging" applies to this phenomenon when the stimulating radiation is optical, "thermoacoustic" is more general term and refers to all radiating sources, including optical.

As used herein, "pulse" refers to the arterial palpation, sometimes tactile, of the heartbeat. The pulse may be palpated in any place that allows an artery to be compressed against a bone, such as at the neck (carotid artery), on the inside of the elbow (brachial artery), at the wrist (radial artery), at the groin (femoral artery), behind the knee (popliteal artery), near the ankle joint (posterior tibial artery), and on foot (dorsalis pedis artery). Pulse (or the count of arterial pulse per minute) is equivalent to measuring the heart rate. The heart rate can also be measured by listening to the heart beat directly (auscultation), traditionally using a stethoscope and counting it for a minute.

As used herein, "reinforcement learning" or "RL" shall refer to a machine learning problem of getting an agent to act in the world so as to maximize its rewards.

As used herein, "representation learning" or "feature learning" shall refer to a set of techniques that learn a feature: a transformation of raw data input to a representation that can be effectively exploited in machine learning tasks. This obviates manual feature engineering, which is otherwise necessary, and allows a machine to both learn at a specific task (using the features) and learn the features themselves: to learn how to learn.

As used herein, "similarity learning" shall refer to an area of supervised machine learning in artificial intelligence that learns from examples a similarity function that measures similarity or relation between two objects.

As used herein, "sparse dictionary learning" shall refer to a representation learning method which aims at finding a sparse representation of input data in the form of a linear combination of base elements as well as those basis elements themselves. These elements are called atoms and they compose a dictionary. Atoms in the dictionary are not required to be orthogonal. This problem setup also allows the dimensionality of representation space to be higher than the one of the input space. The above two properties lead to having seemingly redundant atoms that allow multiple reconstruction ways but also provide an improvement in sparsity and flexibility of the representation.

As used herein, "speckle" is a granular noise that inherently exists in and degrades the quality of an ultrasound signal. The vast majority of surfaces, synthetic or natural, are extremely rough on the scale of the wavelength. Images obtained from these surfaces by coherent imaging systems such as ultrasound suffer from speckle. Speckle is primarily due to the interference of the returning wave at the transducer aperture. Speckle can also represent useful information. For example, difference in speckle characteristics between different tissues could be quantified and the quantified speckle may be useful in the context of the disclosure. Additionally, one skilled in the art may be able to distinguish tissue specific speckle patterns, one from the next.

As used herein, "supervised learning" refers to the machine learning task of inferring a function from labeled training data. The training data consist of a set of training examples. In supervised learning, each example is a pair consisting of an input object (typically a vector) and a desired output value (also called the supervisory signal). A supervised learning algorithm analyzes the training data and produces an inferred function, which can be used for mapping new examples. An optimal scenario will allow for the algorithm to correctly determine the class labels for unseen instances. This requires the learning algorithm to generalize from the training data to unseen situations in a reasonable way.

As used herein, a "support vector machine" or "SVM" or "support vector networks" are supervised learning models with associated learning algorithms that analyze data used for classification and regression analysis. Given a set of training examples, each marked for belonging to one of two categories, an SVM training algorithm builds a model that assigns new examples into one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall on.

As used herein, "vascularization" shall mean the formation of vessels, especially blood vessels. Vascularization may refer to a normal or abnormal or pathological formation of any type of vessel such as blood vessels.

As used herein, "X-rays" comprises X-radiation and refers to a form of electromagnetic radiation loosely having a wavelength ranging from 0.01 to 10 nanometers, corresponding to frequencies in the range 30 petahertz to 30 exahertz ($3 \times 10^{16}$ Hz to $3 \times 10^{19}$ Hz) and energies in the range 100 eV to 100 keV. X-ray wavelengths are shorter than those of UV rays and typically longer than those of gamma rays. In many languages, X-radiation is referred to with terms meaning Röntgen radiation, after Wilhelm Röntgen, who is usually credited as its discoverer, and who had named it X-radiation to signify an unknown type of radiation. Spelling of X-ray(s) in the English language includes the variants x-ray(s), xray(s), and X ray(s). Due to their penetrating ability, X-rays are widely used to image the inside of objects, e.g., in medical radiography and airport security. As a result, the term X-ray is metonymically used to refer to a radiographic image produced using this method, in addition to the method itself.

Ultrasound based measurements of data are important but in order to truly generate a comprehensive data set ultrasound must be able to support the incorporation of other imaging modalities and other physiological measurements, such as, for example, without limitation, X-Ray, fluoroscopy, CT and/or MRI. CT or MRI in conjunction with contrast agents could also be used for lesion detection. Other physiological measurements such as, for example, blood pressure, pulse, BMI, body fat, genetic profiles, saliva assays, blood assays, protein screening and other types of screening may be employed. Indeed, any quantitative or qualitative measurement of disease states may be utilized. Such examples may include, but not be limited to, family history or any other individual previous measurements which may be incorporated in a database and be available to comprise a hyper volume for machine based learning algorithms.

In the present disclosure, systems and methods for using the quantitative aspects of ultrasound imaging along with ancillary data are discussed for providing ailment detection, diagnosis, and treatment. More specifically, ancillary data can be correlated with quantitative ultrasound imaging data to provide ailment detection, diagnosis, and treatment. This is advantageous over current systems and methods using ultrasound imaging which rely on the qualitative aspects of ultrasound imaging to provide ailment detection, diagnosis, and treatment.

Further, in the present disclosure, systems and methods for combining both the quantitative aspects of ultrasound imaging with qualitative aspect of the ultrasound imaging using ancillary data are discussed for providing ailment detection, diagnosis, and treatment. More specifically, quantitative measurements and qualitative measurements taken through ultrasound imaging can be correlated with ancillary data to provide ailment detection, diagnosis, and treatment. This is advantageous over current systems and methods using ultrasound imaging which rely solely on the qualitative aspects of ultrasound images to provide ailment detection, diagnosis, and treatment.

In the present disclosure, systems and methods for combining quantitative aspects of ultrasound imaging along with other non-ultrasound imaging based measurements are discussed for providing ailment detection, diagnosis, and treatment. More specifically, quantitative measurements of ultrasound imaging can be compared to measurements taken using other systems and methods, e.g. non-ultrasound imaging methods and systems, to provide ailment detection, diagnosis, and treatment. This is advantageous over current systems and methods using ultrasound imaging which rely solely on the qualitative aspects of ultrasound images to provide ailment detection, diagnosis, and treatment.

Additionally, in the present disclosure, systems and methods for combining quantitative aspects of ultrasound imaging with past measurements are discussed for providing ailment detection, diagnosis, and treatment. More specifically, past measurement of a current subject or different subjects can be compared to quantitative aspects of current ultrasound imaging for the current subject to provide ailment detection, diagnosis, and treatment. This is advantageous over current systems and methods that use qualitative measurements of ultrasound images to diagnosis ailments regardless of past measurements taken for the same or different subjects.

In the present disclosure, a holistic approach of using a variety of quantitative ultrasound measurements along with other modalities and non-image based measurements generate a hyper volume data set. Hyper planes within this hyper volume data volume set can be used to more accurately describe and track various disease states.

Single measurements can be integrated into a unified approach. Single measurements don't always show disease progression well. While single measurements have sometimes shown promise in describing and predicting severe levels of disease, single measurements can be less accurate in describing or predicting disease during a transition phase. Treating disease during a transition phase, as opposed to when severe levels of disease appear, could be more efficacious. The unified approach described in this disclosure which could incorporate one or many single measurements may be better at analyzing and describing various underlying factors that can produce significant overlap across the progression of disease states.

Other physiological measurements often taken as singular measurements are also described in this disclosure. Methods of acquiring quantitative tissue measurements have been described in the literature but often reported singularly. Singular measurements have resulted in limited success because predicting disease states as only a single item measured in a complex system will not inaccurately describe or predict a disease state accurately. Recent examples include the measurement of stiffness or shear wave velocity to describe disease states of liver, breast, prostate, thyroid and/or other organs. Incorporation of these singular measurements will allow greater accuracy and/or prediction of a disease state.

A variety of quantitative ultrasound measurements along with other modalities and non-image based measurements are described to generate a hyper volume data set where hyper planes within this hyper volume can be used to more accurately describe and track the various disease states. For example, measurement of the degree of liver fibrosis and the disease stages from F0 (healthy) to F4 (severe fibrosis) have current recommended cut off values. While singular cut off values are useful, using them alone to classify or predict disease is inherently flawed and could be misleading and lead to misclassification of a disease state. Misclassification of a disease state, especially at an early stage, could harm a patient by not allowing them to receive an accurate diagnosis and treatment when they need it most. Misclassification of a disease state could also ultimately lead to an inappropriate treatment and a greater burden to the health care system. Besides the cut off values, a number of other factors may also bias results and should be considered. Such other factors may include, for example, without limitation, blood pressure, last meal, fat deposits, measurement position, and pressure of the transducer, etc. Methods and systems can be utilized to predict a disease state using, for example, the cut off values and at least one of the other factors employing a more holistic approach.

The systems and methods have the potential to be configured to collect any subset of the datasets mentioned herein and not require a complete set in order to be useful in the diagnostic process of the learning algorithm. Datasets would have the ability to be uploaded into the cloud and aggregated across many sites as well as have the potential to be made available to researchers for development of personalized algorithms. The basic types of algorithms that could be developed from the aggregated data sets could include, for example, decision tree based, associated rule based learning, artificial neural networks, inductive logic, support vector(s), clustering, Bayesian networks, reinforcement learning, representation learning, similarity and metric learning, sparse dictionary learning, genetic algorithms and/or such other algorithms. Those skilled in the art of machine-based learning techniques would recognize that this is only a subset of the types of techniques that could be applied to a data set as described above. Also, each of the algorithms would continue to be enhanced as additional data is contributed to the master database.

For classification of a disease state, core biopsy has traditionally been used as the "gold standard," and methods are often judged with respect to how well they correlate to core biopsy. However, core biopsy has several drawbacks, which include limited sample size, pain to recipient, potential infection, as well as others. The description set forth herein is meant to alleviate some of these shortcomings.

The description set forth herein comprises systems and methods that for generating multiple measurements via ultrasound and includes and incorporates other measurements from other modalities to generate a database that stores the information. The description set forth herein also describes incorporates core biopsies to generate a data set. That data set can, for example, be used as a training set for machine learning algorithm generation used to predict the disease state of new subjects without correlating core biopsy data. A patient may, therefore, avoid some of the drawbacks of core biopsy mentioned herein, such as limited sample size, pain, potential infection, etc.

Ultrasound measurements used in this description can comprise tissue stiffness, sound velocity propagation, attenuation, non-linear wave generation properties, speckle statistics, vascularization measurements/properties form (CEUS micro bubbles or photoacoustics), and tissue composition through photoacoustics. One skilled in the art would readily appreciate that other measurements may be used.

One skilled in the art would understand that there are several documented methods of making measurements and each has tradeoffs. The ability to capture and store raw data (transducer element data, for example) along with system parameters and/or configuration can allow future enhancements as data can be utilized to improve each measurement or generate new quantitative measurements as new algorithms are created. As such, an entire dataset can be kept and associated with a patient. In another embodiment less than an entire dataset is stored but one would still be able to mine measured parameters.

Some of the infrastructure that can be used with embodiments disclosed herein is already available, such as general-purpose computers, ultrasound imaging systems, computer programming tools and techniques, digital storage media, and communications networks. A computing device may include a processor such as a microprocessor, microcontroller, logic circuitry, or the like. The processor may include a special purpose processing device such as an ASIC, PAL, PLA, PLD, FPGA, or other customized or programmable device. The computing device may also include a non-transitory computer-readable storage device or medium, such as non-volatile memory, static RAM, dynamic RAM, ROM, CD-ROM, disk, tape, magnetic, optical, flash memory, or other computer-readable storage medium.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

Figure 1:
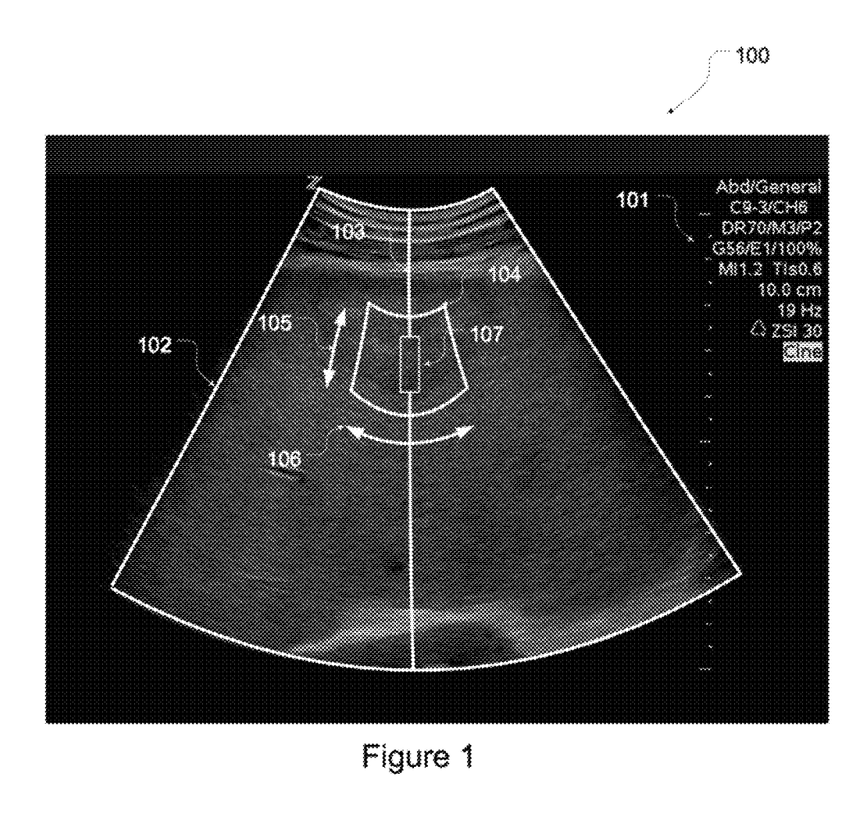
FIG. 1 shows an ultrasound B-mode image of an adult liver.

FIG. 1 shows an ultrasound B-Mode image 101 with the associated attributes and graphical indicators for an adult liver for the purpose of collecting data that can be used for quantitative and/or qualitative parameter extraction.

The image 100 has a section 101 indicating parameters used to gather the information. The full field of view 102 and region of interest or regional measurement area 104 are shown. A line 103 indicates where the normal to transducer interface occurs. The region of interest 104 may be moved in an axial 105 or lateral 106 way for accurate placement. A smaller area 107 may be placed within the field of view 102 or region of interest 104 for single point estimations of quantitative values.

More specifically, the image 100 has a section 101 that depicts the parameters being used to gather the information. These parameters would at a minimum contain transducer type, imaging frequency/settings, dynamic range settings, map setting, persistence setting, gain setting, edge setting, acoustic output power, mechanical index, thermal index, depth and frame rate. Other parameters are usually present. The additional parameters that might be also included in this set could be the (ZONE Speed Index) ZSI, shear wave velocity, non-linear B/A ratio and tissue attenuation properties, among others. Parameters would may not only be shown on the image but would also be collected and stored in a raw format (unprocessed) in the image data archive along with the associated system settings so that the measurements could be recalculated at a later time if needed or different algorithms could also be investigated at future dates.

A first type of data is measured from basic underlying images and as such is applicable to the full field of view 102. Measurements that are associated with the full field of view 102 might be basic speckle statistical distribution, general backscatter properties, attenuation, non-linear B/A ratio and kinetics of the vascular structure with the use of CEUS, among others. These measurements might not be calculated from the actual data displayed on the image as this data has been optimized for the viewer. Rather, the data that most likely would be used as the starting point for these types of parameter extraction(s) may be either the non-detected in-phase and quadrature data set or the channel element data from each transmit/receive cycle and every transducer element used in the generation of the image frame. In addition to a single frame of data, one may want to store several frames of data, such as those both before and after the frame of the actual data set from which extraction occurs as some of the measurements might be able to be improved by looking across multiple frames that have a high level of anatomic correlation but should be uncorrelated from other noise sources.

A second type of data that could be collected is that which might be extracted from a region of interest 104. These types of measurements could also include the type of measurements that could be made from an entire field of view 102 but contain items that might not be practical given other tradeoffs like acoustic power, temperature rise of the transducer or items that require a different type of transmit/receive structure or wave profile to improve overall accuracy of the calculation. A couple of these types of measurements might be, for example, without limitation, shear wave velocity estimation or tissue attenuation estimation.

It is also possible to obtain measurements using energy sources other than sound waves. One could, for example, without limitation, use a laser to investigate the ox/deox vascular structure within a region of interest 104 employing photoacoustics and limiting the region of interest 104 to near the transducer, if necessary. Such a technique could provide a fine detailed structure of overall vascular structure and properties and ultimately be used to predict disease states. A region of interest 104 can be moth resized as well as moved in an axial 105 or lateral 106 direction so that it can be accurately placed. The type of measurements derived from a region of interest 104 can be displayed via a color-coded map or the user can select a sub region and the basic statistics of the sub region can be displayed (e.g., without limitation, mean, std, etc.).

When making measurements in a regional measurement area or region of interest 104, there might be some tradeoffs so that a full field of view 102 can maintain some level of performance and not be optimized for a main area. Thus, a third type of data that could be collected involves a quantitative measurement around a smaller area 107 used for single point estimations of quantitative values. These estimations could be any of those mentioned herein. The smaller area 107 can be positioned anywhere within the full field of view 102. A line 103 indicates where the normal to the transduce interface occurs so the user can have a visual representation of the area the measurement occurred. As with all measurements for the full field of view 102 to the variable area based region of interest 104 to the small area 107 the underlying raw data is stored so that it is available for further research and potential parametric extraction. This data set also contains all the necessary parameters so that the system would have the capabilities to re-extract all of the quantitative estimates from the raw data if needed. It should be noted that there are several other methods of quantitative measurements that can be made with ultrasound equipment.

The image 100 can represent a quantitative view of measurements of an ultrasound image. Quantitative measurements, as used herein, can include specific quantities or numerical values for forming quantitative information, e.g. for a subject. Additionally, quantitative measurements can be specific to ultrasound imaging. For example, quantitative measurements can include signal strengths of received echoes in an ultrasound image. Quantitative measurements can also be specific to non-ultrasound imaging. For example, quantitative measurements can include quantities about a BMI for a subject. Quantitative measurements can form all or portions of quantitative information and quantitative information derived from ultrasound imaging, as described herein.

The image 100 can indicate a qualitative view of qualitative measurements of an ultrasound image. Qualitative measurements, as used herein, can include specific non-numerical information, otherwise non-numeric information, e.g. for a subject. For example, qualitative measurements can include selected portions of an ultrasound image, e.g. built from quantitative measurements for the ultrasound image. In another example, qualitative measurements can include non-numeric measurements of a subject outside of numerical representations, e.g. a display of an EKG reading of a subject.

Either or both quantitative measurements and qualitative measurements can be used along with ancillary information to diagnose, treat, and prevent ailments in subjects. Ancillary information, as used herein, can include information separate from qualitative measurements and/or quantitative measurements. More specifically, ancillary information can include information for another subject, or built thereon for purposes of diagnosing, treating, and preventing ailments in a subject. For example, ancillary information can include a disease symptom map for patients with a specific disease.

A disease state of a subject can be determined by correlating one or a combination of quantitative information, qualitative information, and ancillary information. More specifically, a disease state of a subject can be determined by combining or otherwise comparing values defined by one or a combination of quantitative information, qualitative information, and ancillary information. For example, a disease state can be determined by correlating quantitative information with ancillary information by comparing the information or combining values derived from the information. In another example, a disease state can be determined by correlating quantitative information and qualitative information by comparing the information or combining values derived from the information.

Figure 2:
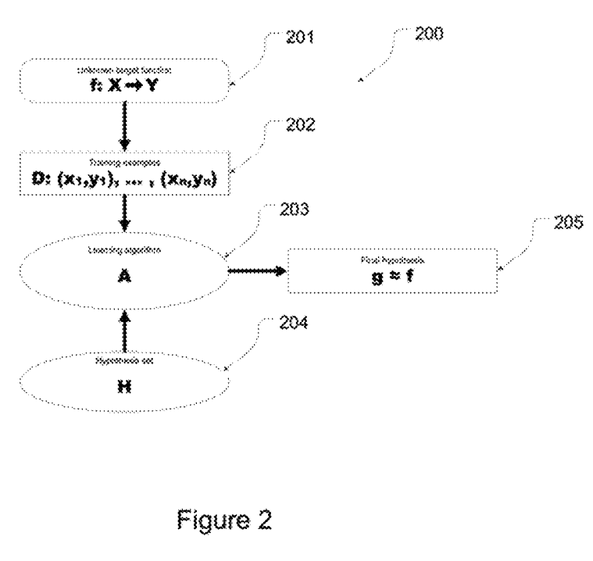
FIG. 2 shows a flow diagram of potential machine learning algorithm for the classification of various disease states based on quantitative values.

FIG. 2 shows an example of a flow diagram of a potential machine-learning algorithm 200 for the classification of various disease states based on quantitative values. An unknown target function 201 based upon a training set or training examples 202 are passed through a learning algorithm 203, which may be selected from a hypothesis set 204 of possible learning algorithms. A final hypothesis 205 may be generated.

An algorithm is generalized for trained or supervised learning to correlate an unknown target function 201 based on a training set or training examples 202 collected from patient data classified by a standard of classification. Standards of classification can be related to or be based upon any, all or more of core biopsy, blood pressure, pulse, BMI, body fat, angiography, blood analysis, saliva analysis, photoacoustic imaging, protein screening and genetic screening.

In one embodiment, the standard of classification is biopsy. Training set or training examples 202 is passed through a learning algorithm 203 that is selected from a hypothesis set 204 of potential learning algorithms. The hypothesis set 204 could contain a variety of methods. Possible examples include, without limitation, decision tree learning, association rule learning, artificial neural networks, inductive logic, support vector, clustering, Bayesian networks, reinforcement learning, representation learning, similarity and metric learning, sparse dictionary learning, and any other type of algorithms, such as, for example, genetic algorithms. A mixture of methods could also be used. For example, without limitation, a decision tree learning algorithm could be used for course classification and then a neural network method could be used after course classification.

Figure 3:
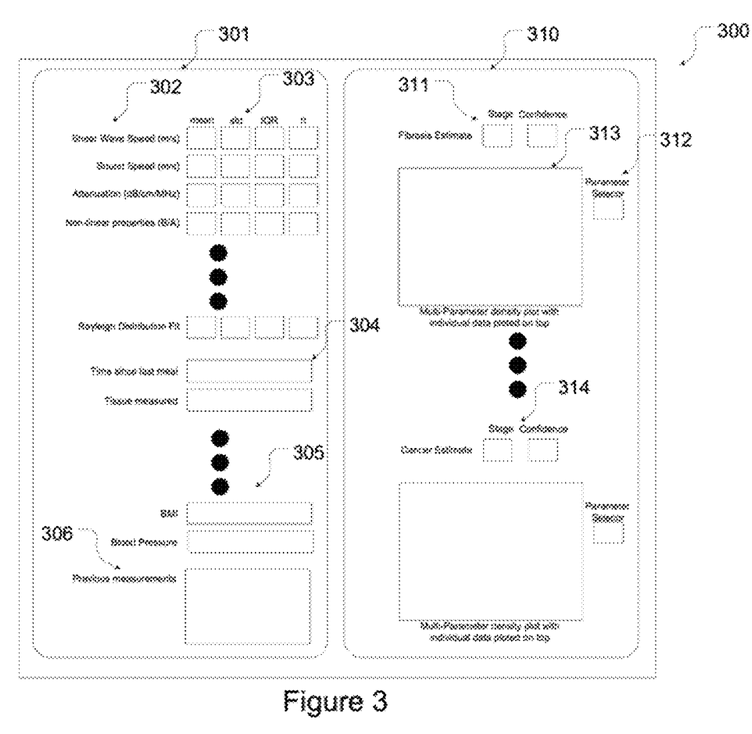
FIG. 3 shows an example of a calculation, measurement, and report page.

FIG. 3 shows an example of a calculation, measurement, and report page 300 for the communication of quantitative measurement set and hypothesized results. Exemplary information measurement section 301 shows measurements taken from ultrasound 302 along with statistical aspects 303 if multiple measurements are made. Information specific to individual 304, such as last meal time may be included. Other physical qualities of the individual 305 or previous measurements and data related to the individual 306 may be included. A hypothesis section 310 may be generated and displayed. Certain types of disease, such as liver fibrosis or cancer may be reported in a fibrosis estimate or cancer estimate 314, respectively. A parameter selector 312 or multi-parameter density plot 313 may be included.

An exemplary information measurement section 301 displays information and measurements and a hypothesis section 310 displays hypothesis. In the information measurement section 301 there are measurements taken from ultrasound 302 along with statistical aspects 303 if multiple measurements are made. Each measurement could be linked to a representative image that could be reviewed if an examiner desired to get a better understanding of the landscape from which quantitative information is derived. Data contained in the information measurement section 301 is not limited to data from an imaging modality like ultrasound, CT, MRI, X-Ray, flouroscopy, angiography, etc. but may also include information specific to the individual 304 such as, for example, time since last meal. There may also be a section for reporting other physical quantities of the individual 305. Other physical quantities of the individual 305 could include, for example, without limitation, BMI, blood pressure, blood assay results, protein screening results, genetic profiles and the like along with other previous measurements and data related to the individual 306 as well as their outcomes. Thus, any and all information in the information measurement section 301 is capable of being used as an input to generate a hypothesis of the overall patient state in the hypothesis section 310.

In the hypothesis section 310, information in the information measurement section 301 can be used with, for example, underlying raw data used to obtain various values from the database of all previous patients that have been collected to generate a hypothesis of the overall disease state being investigated. For example, without limitation, one type of disease state that could be reported might be liver fibrosis or cancer, which could be reported in a fibrosis estimate 311 or cancer estimate 314, respectively. Other disease states besides liver fibrosis and cancer may be envisioned by one skilled in the art and are intended to be within the scope of the description. As an example, information contained in the hypothesis for liver fibrosis would be the current stage of estimated fibrosis (F0, F1, F2, F3 or F4).

It would also be desirable to be able to associate a level of confidence along with the estimate. Depending on the estimate and confidence a user could look at multiple sections of parameters used to generate the estimate in a parameter selector 312. A parameter selector 312 may have the ability to generate a multi-parameter density plot 313 with an individual's data plotted on top so that a reviewer would be able to understand how the quality of each parameter was as compared to other individuals with known classifiers of an examined disease state.

The hypothesis section 310 would not be limited to being able to estimate a single type of disease and disease state but could also have the ability to estimate the change of additional diseases as well. In addition, in order to obtain an hypothesis of the disease state it is not necessary that the information measurement section 301 be a complete set of data as in most cases the information measurement section 301 will only be sparsely populated and the associated database of information that is used to generate the hypothesis section 310 should be capable of still extracting an estimate from a sparse data set.

Figure 4:
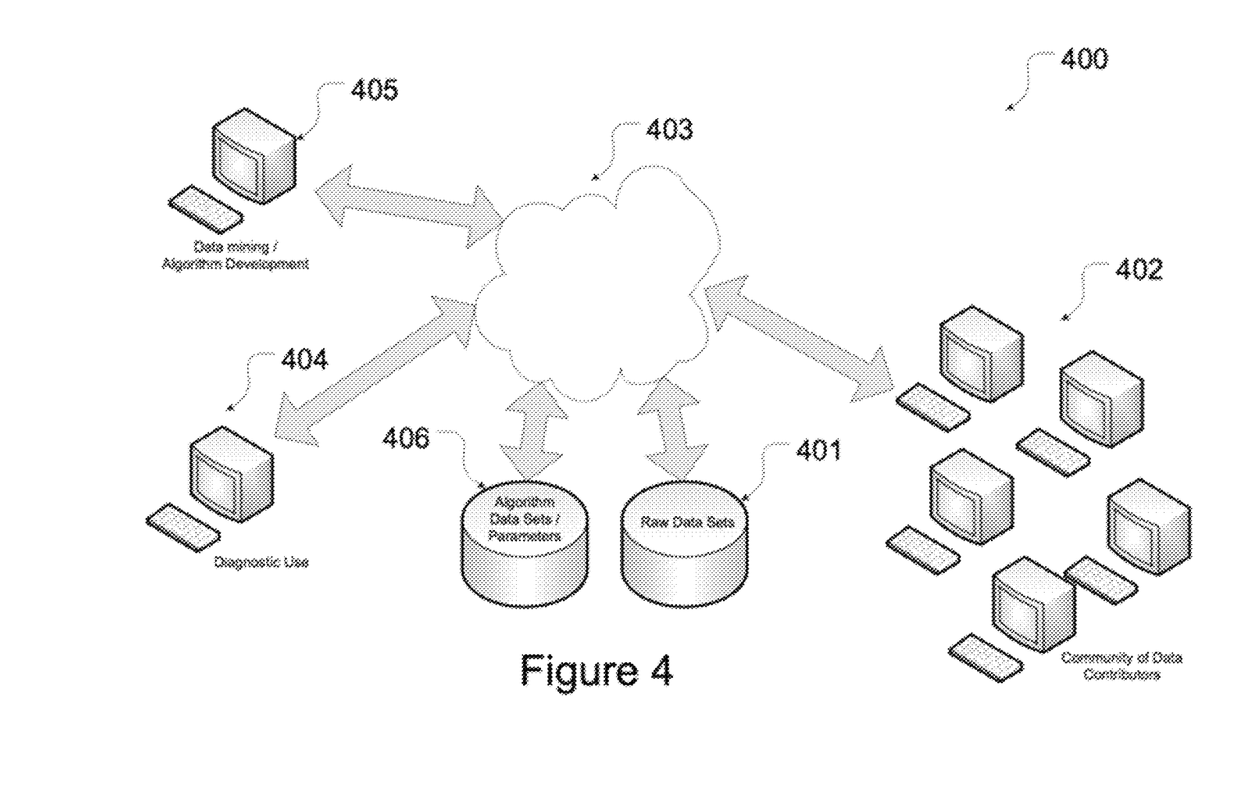
FIG. 4 shows an example diagram of data collection, storage, distribution, use, and algorithmic learning.

FIG. 4 shows an example diagram of data collection, storage, distribution, use and algorithmic learning 400. Raw data sets 401 can be associated with a community of data users 402 contributed via a cloud based system 403. An exemplary data base could contain, for example, algorithm data sets and parameters 406 as well as diagnostic use 404 and data mining and algorithm development 405.

When collecting data for machine learning applications it is desirable to acquire data sets across many communities of users as well as across several populations of patients so that a sufficiently diverse set of data is collected and any single group of systematic biases do not result in skewing predictive results. A cloud based system 403 may be associated with a community of data users 402 contributing data via the cloud based system 403 to a database of raw data sets 401. The raw data sets 401 can then be accessed via the cloud based system 403 for data mining and algorithm development 405. These potential algorithms and results can then be transferred back through the cloud based system 403 to a database that contains the algorithm data sets and parameters 406. Algorithm data sets and parameters 406 can be stored and/or associated with the raw data sets 401 but have been depicted separately for simplicity in FIG. 4. Once the algorithm data sets and parameters 406 have been generated a diagnostic user 404 can download information via the cloud based system 403 to generate disease hypothesis. The data set of information that the diagnostic user 404 has used with the algorithm data sets and parameters 406 for disease hypothesis can then be uploaded from cloud based systems 403 to the raw data sets 401 to continue to accumulate data for future users for data mining and algorithm development 405. It should be noted that raw data sets 401 may be sparse in their data fields as it would be unrealistic to expect that all of the community of data contributors 402 would always generate a complete and sufficient set of data for each individual study. It also allows for the addition of new fields of data to be included in the raw data sets 401 and will not compromise the utility of the historical information contained in the previously collected raw data sets 401.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles described herein. The scope of the present invention should, therefore, be determined only by the following claims.

The invention claimed is:

1. A method comprising:
    identifying at least one quantitative measurement of a subject using ultrasound imaging, the at least one quantitative measurement included as part of quantitative information of the subject gathered based on the ultrasound imaging;
    comparing the at least one quantitative measurement to a first predetermined standard to determine a first initial value, the first predetermined standard included as part of ancillary information to the quantitative information of the subject and qualitative information of the subject and falling within a first range of quantities;
    comparing at least one previous measurement of disease to a second predetermined standard to determine a second initial value, the second predetermined standard included as part of the ancillary information and falling within a second range of quantities; and
    correlating the quantitative information and the at least one previous measurement with the ancillary information using the first initial value and the second initial value to determine a final value that is used in predicting at least one of a presence or progression of a disease state of the subject.

2. The method of claim 1, wherein the at least one quantitative measurement included as part of the quantitative information is an ultrasonic quantitative measurement formed from contrast-enhanced ultrasound, photo-acoustic imaging, acoustic radiation force impulse imaging, ultrasonic characterization of non-linear properties, ultrasonic attenuation, ultrasonic sound speed characterizations and/or ultrasonic speckle statistics.

3. The method of claim 1, wherein the at least one previous measurement is an ultrasonic qualitative measurement derived from contrast-enhanced ultrasound, photo-acoustic imaging, acoustic radiation force impulse imaging, ultrasonic characterization of non-linear properties, ultrasonic attenuation, ultrasonic sound speed characterizations and/or ultrasonic speckle statistics.

4. The method of claim 1, wherein the at least one previous measurement is a measurement of at least one of a core biopsy, blood pressure, metabolic rate, pulse, BMI, body fat, angiography, blood analysis, saliva analysis, photo-acoustic imaging, protein screening and genetic screening.

5. The method of claim 1, wherein the at least one previous measurement is identified using a method other than the ultrasound imaging.

6. The method of claim 1, further comprising using other imaging modalities to determine the final value that is used in predicting the disease state of the subject.

7. The method of claim 6, wherein the other imaging modalities include one of core biopsy, X-rays, fluoroscopy, computed tomography or MRI.

8. The method of claim 1, further comprising using raw data to determine the final value that is used in predicting the disease state of the subject.

9. The method of claim 1, further comprising using a machine-learning algorithm to predict the disease state of the subject.

10. The method of claim 9, wherein the machine-learning algorithm is maintained using at least one of decision tree learning, association rule learning, artificial neural networks, inductive logic, a support vector, clustering, Baysian networks, reinforcement learning, representation learning, similarity and/or metric learning, sparse dictionary learning and/or protein and/or genetic algorithms.

11. A system comprising:
    one or more processors; and
    at least one computer-readable storage medium having stored therein instructions, when executed by the one or more processors, cause the one or more processors to perform operations comprising:

identifying at least one quantitative measurement of a subject using ultrasound imaging, the at least one quantitative measurement included as part of quantitative information of the subject gathered based on the ultrasound imaging;

comparing the at least one quantitative measurement to a first predetermined standard to determine a first initial value, the first predetermined standard included as part of ancillary information to the quantitative information of the subject and qualitative information of the subject and falling within a first range of quantities;

comparing at least one previous measurement of disease to a second predetermined standard to determine a second initial value, the second predetermined standard included as part of the ancillary information and falling within a second range of quantities; and correlating the quantitative information and the at least one previous measurement with the ancillary information using the first initial value and the second initial value to determine a final value that is used in predicting at least one of a presence or progression of a disease state of the subject.

12. The system of claim 11, wherein the at least one quantitative measurement included as part of the quantitative information is an ultrasonic quantitative measurement formed from contrast-enhanced ultrasound, photo-acoustic imaging, acoustic radiation force impulse imaging, ultrasonic characterization of non-linear properties, ultrasonic attenuation, ultrasonic sound speed characterizations and/or ultrasonic speckle statistics.

13. The system of claim 11, wherein the at least one previous measurement is an ultrasonic qualitative measurement derived from contrast-enhanced ultrasound, photo-acoustic imaging, acoustic radiation force impulse imaging, ultrasonic characterization of non-linear properties, ultrasonic attenuation, ultrasonic sound speed characterizations and/or ultrasonic speckle statistics.

14. The system of claim 11, wherein the at least one previous measurement is a measurement of at least one of a core biopsy, blood pressure, metabolic rate, pulse, BMI, body fat, angiography, blood analysis, saliva analysis, photo-acoustic imaging, protein screening and genetic screening.

15. The system of claim 11, wherein the at least one previous measurement is identified using a technique other than the ultrasound imaging.

16. The system of claim 11, wherein the instructions, when executed by the one or more processors, cause the one or more processors to perform operations further comprising using other imaging modalities to determine the final value that is used in predicting the disease state of the subject.

17. The system of claim 16, wherein the other imaging modalities include one of core biopsy, X-rays, fluoroscopy, computed tomography or MRI.

18. The system of claim 11, wherein the instructions, when executed by the one or more processors, cause the one or more processors to perform operations further comprising using raw data to determine the final value that is used in predicting the disease state of the subject.

19. The system of claim 11, wherein the instructions, when executed by the one or more processors, cause the one or more processors to perform operations further comprising using a machine-learning algorithm to predict the disease state of the subject.

20. The system of claim 19, wherein the machine-learning algorithm is maintained using at least one of decision tree learning, association rule learning, artificial neural networks, inductive logic, a support vector, clustering, Baysian networks, reinforcement learning, representation learning, similarity and/or metric learning, sparse dictionary learning and/or protein and/or genetic algorithms.

* * * * *